United States Patent [19]
Mehkeri et al.

[11] Patent Number: 5,512,491
[45] Date of Patent: Apr. 30, 1996

[54] METHOD FOR ULTRA-TRACE LEVEL ANALYSIS OF WATER

[75] Inventors: K. Anwer Mehkeri, Aylmer; Abdul Malek, Brossard; Bryan R. Hollebone; Xinqiang Zhou, both of Ottawa, all of Canada

[73] Assignee: Areco Canada Inc., Nepean, Canada

[21] Appl. No.: 139,107

[22] Filed: Oct. 21, 1993

[30] Foreign Application Priority Data

Apr. 8, 1993 [CA] Canada ................................. 2093676

[51] Int. Cl.$^6$ .............................. G01N 1/00; G01N 33/20
[52] U.S. Cl. .......................... 436/177; 210/662; 210/692; 436/73
[58] Field of Search ................................ 436/73, 161, 77, 436/81, 83, 91, 93, 125, 126, 131, 146, 177, 140, 524, 525, 527, 528, 529, 530, 531; 73/61.41, 61.42; 422/69; 210/662, 687, 691–692

[56] References Cited

U.S. PATENT DOCUMENTS

| | | | |
|---|---|---|---|
| 3,667,607 | 6/1972 | Brandt | 210/198.1 |
| 3,847,550 | 11/1974 | Scott et al. | 436/161 |
| 3,877,878 | 4/1975 | Kerfoot et al. | 422/100 |
| 4,405,493 | 9/1983 | Pippard | 422/12 X |
| 4,917,806 | 4/1990 | Matsunaga et al. | 210/662 |
| 4,999,306 | 3/1991 | Yafuso et al. | 436/68 |
| 5,133,901 | 7/1992 | Peterson et al. | 209/3.2 |
| 5,192,691 | 3/1993 | Quinn et al. | 436/161 |
| 5,223,153 | 6/1993 | Lawson et al. | 210/778 |
| 5,227,311 | 7/1993 | Kuemmerle et al. | 436/76 X |

FOREIGN PATENT DOCUMENTS 1507904  12/1967  France.

OTHER PUBLICATIONS

Krishnaswami et al. "Silicon, Radium, Thorium, and Lead in Seawater . . . " *Earth and Planetary Science Letters* 16 (1972) 84–90.

"Adsorption/Coprecipitation of Trace Elements From Water With Iron Hydroxide". Leckie et al, Sep. 1980.

Fou. "Water Purity Investigation Using Proton Induced X–Ray Emission". *Nuclear Instruments and Methods*, vol. 186, pp. 599–604, 1981.

Klavinis et al. "Determination of metal species in surface waters" *Latv. Kim. Z.* vol. 6, pp. 702–706, 1992.

Hiraide et al. "Speciation of iron in river water" *Anal. Sci.*, vol. 4(6), pp. 605–609, 1988.

Hiraide et al. "Separation and determination of Chromium (VI) anions" *Fresenius' Z. Anal. Chem.* vol. 335(8), pp. 924–926, 1989.

*Primary Examiner*—Robert J. Warden
*Assistant Examiner*—Robert Carpenter
*Attorney, Agent, or Firm*—David J. French

[57] ABSTRACT

A method for ultra-analysis of water for trace impurities. An effective trapping media functions by binding gels that carry ultratrace analytes on their surfaces.

18 Claims, 5 Drawing Sheets

METHOD FOR ULTRA-TRACE LEVEL ANALYSIS OF WATER

FIELD OF THE INVENTION

This invention relates to the analysis of water to detect the presence of minute amounts of trace contaminants—"ultra-trace level analysis". More particularly, it relates to a procedure and materials for the preconcentration of analytes in order to facilitate the analytic process.

BACKGROUND OF THE INVENTION

Ultra-trace level analysis, when applied to the testing of water, entails endeavouring to identify and measure the quantities of non-aqueous components of water, "analytes", that are present at levels of generally parts per billion or trillion, or less. Such analytes are either dissolved in water as molecules and ions are adsorbed on extraneous particulates and/or colloidal matter usually present in water or, in the case of organic micro-organisms, are in suspension. Thus, trace contaminants in water are distributed between dissolved and non-dissolved components.

This invention relates to analyzing the non-dissolved component of contaminants in fresh, or non-saline water. (Further reference to water herein is directed to non-saline water.) It also relates to analyzing dissolved components in certain cases where such components may be forced to precipitate from solution.

In general, the most toxic contaminants for chronic diseases present at ultra-trace levels in water are in the non-dissolved form. If a complete analysis of a water sample is required, the contaminants remaining in the permeate, principally those dissolved in the aqueous phase, may also be extracted by means of adsorption on a resin column following standard techniques. However, often it is sufficient to only analyze for the presence of the non-dissolved fraction.

To carry-out ultra-trace level analysis on water it is essential to sample sufficient volumes of water in order to collect a detectable quantity of contaminants. The cost of analysis increases when only smaller quantities of samples are available for testing. Therefore, the accumulation of large sample quantities will reduce costs and increase the number of techniques available to effect analysis. Accumulation of trace samples of micro-organisms will also allow identification through culturing samples to be effected more reliably.

Difficulties arise in applying most normal trapping techniques, such as filtration and adsorption, to the ultra-trace analysis of the non-dissolved components in surface or waste water. When suspended matter is present it is typical that only a relatively small volume of water can be made to flow readily through the normal sieve-type filter medium or the barrier-type filters used in ultra-trace filtration. This is because such filters have very fine pore dimensions, plug-up easily, and rapidly develop a high back-pressure. These are not convenient characteristics when it is intended to filter large volumes of water.

Depth-filters are less susceptible to blockage than barrier filters. Known depth-filters, on the other hand, are composed of random mats of polymeric materials and rely on the density and thickness of the mats to trap particles. These filters are generally capable of retaining larger quantities of particles within their matrices and this makes filtration of large volumes of fluids more practical. However, such filters are not efficient at trapping micron-level sized particles and colloids. Moreover, commercially available depth-filters usually contain contaminating binders that bleed during extraction of the analytes and thereby complicate analytical procedures.

Both sieve and depth filters of conventional design need to be of unwieldy size to be able to sample large volumes of turbid fluids.

Adsorption columns perform poorly as filters and have limited capacity to trap analytes. The consequence is that large volumes of adsorbers must be used if adsorption columns are to be used to collect significant quantities of analytes.

A further concern with adsorbers is that an extraction process is required to recover the analytes. The adsorber then contributes contaminants to the extract at levels which interfere with ultra-trace analysis. This inherent contamination problem persists in spite of extensive cleaning.

An unappreciated aspect of ultra-trace analysis as applied to fresh water is that many ultra-trace analytes have not been reliably quantified because they are entrained within metal hydroxyl colloids such as alumina silica colloids. Colloids create a problem in filters in that they readily block filter pores, thus limiting sample quantities. Consequently, to collect convenient quantities of colloidally-trapped analytes, large filter areas are required. Larger filters increase contamination.

In the case of adsorbers, while their poor recovery ratios have been recognized, there has apparently been little or no appreciation of the fact that adsorbers must compete with the binding capacity of colloids in order to accumulate trace analytes.

Accordingly, it is desirable to develop a compact form of a binder-free analytical trapping medium that will allow the extraction of ultra-trace level quantities of non-dissolved analytes found in non-saline water. Further, it is desirable to collect such analytes in concentrations that will make analysis convenient.

A further advantageous procedure when large volumes of water are being sampled, would be to limit the sampling time to only that required to produce a level of accumulated analytes susceptible to convenient detection.

It is on the basis of this background that the present invention is directed to improving the procedure by means of which ultra-trace analysis of large volumes of water may be carried-out.

The invention in its general form will first be described, and then its implementation in terms of specific embodiments will be detailed with references to the drawings following hereafter. These embodiments are intended to demonstrate the principle of the invention, and the manner of its implementation. The invention will then be further described, and defined, in each of the individual claims which conclude this Specification.

SUMMARY OF THE INVENTION

According to the invention in its broadest sense, improved analytical trapping media have been devised by forming a three dimensional, depth-filter matrix of micro-porous adsorbent material that will provide substantially irreversible binding sites for the entrapment of colloidal carriers and analytes present in non-saline water. After exposure of such media to water which is to be sampled, ultra-trace analysis may be carried-out either directly on the analytes entrained within the entrapped colloidal carriers (e.g. by spectroscopy techniques), or by extraction.

The trapping media may comprise a variety of microporous materials that present "active" hydroxyl groups over the surface of such material. "Active" hydroxyl groups are those capable of forming new bonds with the hydroxyl-bridges found within the colloidal carriers. This is effected through the release or elimination of a hydrogen ion.

Such hydroxyl groups may be formed on the surfaces of both organic and inorganic materials. An inorganic example would be a micro-porous support coated with freshly-prepared aluminum hydroxide. Suitable supports include zeolites, kieselghur, fuller's or diatomaceous earth, alumina and silica gel. A calcined diatomaceous earth product produced by John Mansville Corporation and sold under the trade mark CELITE is moderately directly effective in this procedure as it contains active hydroxyl groups in its natural form when hydrated and has a high internal surface area with voids that readily accommodate colloidal material. CELITE, as with the other referenced micro-porous inorganic materials, will perform in a superior manner if treated to add hydroxyl groups as described above.

An organic example of a suitable trapping media is the range of porous materials originating from Pharmacia Incorporated of New Jersey and sold under the trade mark SEPHADEX. This material is a polymerized polysaccharide in the form of beads. Specified pore-sizes can be prepared as required, ranging from 100 to 1 million Daltons. This material contains naturally "active" hydroxyl groups as part of the sugar structure.

Trapping media provided with active hydroxyl groups have the valuable feature that the colloidal carriers become irreversibly bound in the media. It is believe that this occurs due to a chemical reconstruction process in which they become bound to the hydroxyl groups. This is suggested by the fact that it has been found that for each ion of the colloid which is bound, a hydrogen ion is released in its typically hydrated form known as a "hydronium ion". Under electron-microscopy, the immobilized colloidal gel can actually be seen accumulated within the pores of the trapping media.

It appears, therefore, that the dissociation constant for the colloidal gels, once absorbed, has been reduced by many orders of magnitude compared to trapping on conventional adsorber materials such as AMBERLITE (trade mark) resins.

The analytes collected on the basis of this invention may be extracted from the trapping media by known procedures. Once extracted, they may be analyzed by known techniques to determine their character and quantity. In this manner the ultra-trace analysis of the original volume of water that passed through the depth-filter may be completed. Because no binders are employed in the preferred embodiment, such chemicals are not present to interfere with the process of analysis.

The efficiency of the trapping of the heavy metals within trapping media can be influenced by adjusting the pH of the water sample being fed to the trapping media. The pH may be adjusted to the optimum values for effecting the precipitation, as hydroxides, of the metal, or groups of metals being isolated.

The method of the invention makes possible the ultra-trace analysis of contaminants of greatest concern to society, e.g. the detection of hydrophobic organic substances and insoluble hydroxides of heavy metals. Examples include polychlorinated biphenyls (PCB's), dioxins, furans, polycyclic aromatic hydrocarbons (PAH's), lead, chromium, cadmium, mercury, etc. The filter medium of the invention will also accumulate and concentrate bacterial, protozoa, diatoms and other microbiota.

A convenient method of analysis for the presence of heavy metals in the trapping media is by X-ray fluorescence (XRF). This technique will identify both an element and its quantity, while it is still entrained within the trapping media. XRF analysis is convenient because it is inexpensive and portable. The use of XRF is made possible because of the relatively large quantities of analytes made available for analysis by the preconcentration method of the invention.

For XRF to be utilized, the trapping media must be sufficiently X-ray transparent. It is ideally suited where an organic trapping media is employed. Where less transparent inorganic trapping media are used, analytes and heavy metals can often still be detected using back-scatter compensation.

A further advantage of the trapping media of this invention arises from its efficiency in removing suspended matter from the water. Subsequent analysis of the permeate for dissolved material is simplified because of the reduced incidence of contamination from suspended matter.

The foregoing summarizes the principal features of the invention. The invention may be further understood by the description of the preferred embodiments, in conjunction with the drawings, which now follow.

The invention in its general form will first be described, and then its implementation in terms of specific embodiments will be detailed with reference to the drawings following hereafter. These embodiments are intended to demonstrate the principle of the invention and the manner of its implementation. The invention will then be further described, and defined, in each of the individual claims which conclude this Specification.

DESCRIPTION OF THE PREFERRED EMBODIMENTS

Figure 1:
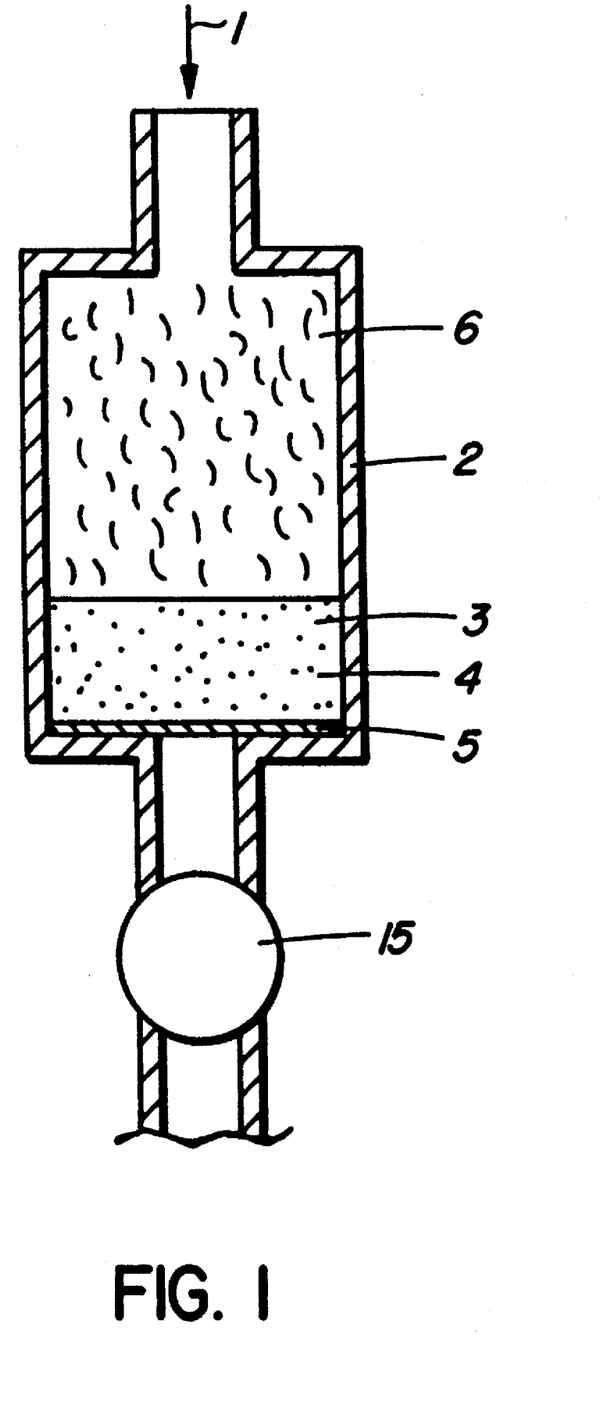
FIG. 1 is a schematic depiction of a basic continuous-flow system for trapping contaminants in fresh water.

In FIG. 1 a flow of water 1 enters a cylinder 2 containing a column 3 of trapping media 4 supported on filter paper 5. Above the media 4 is a glass fiber matrix 6 for the removal of larger sized particulates. In a preferred embodiment the trapping media 4 is CELITE (trade mark) upon whose surfaces has been deposited, preferably, a thin layer of freshly-prepared aluminum hydroxide. Alternately, magnesium hydroxide, for example could be deposited if it was desired to test for aluminum compounds as an analyte. A meter 15 registers the flow of water 1.

The column 3 receives the flow of water 1 in the manner of a depth filter. Colloids, typically aluminum sulphate colloids, become bound to the surface and within the pores of the trapping media 4. Analytes within the colloids thereby become immobilized and accumulate within the trapping media 4.

Figure 3:
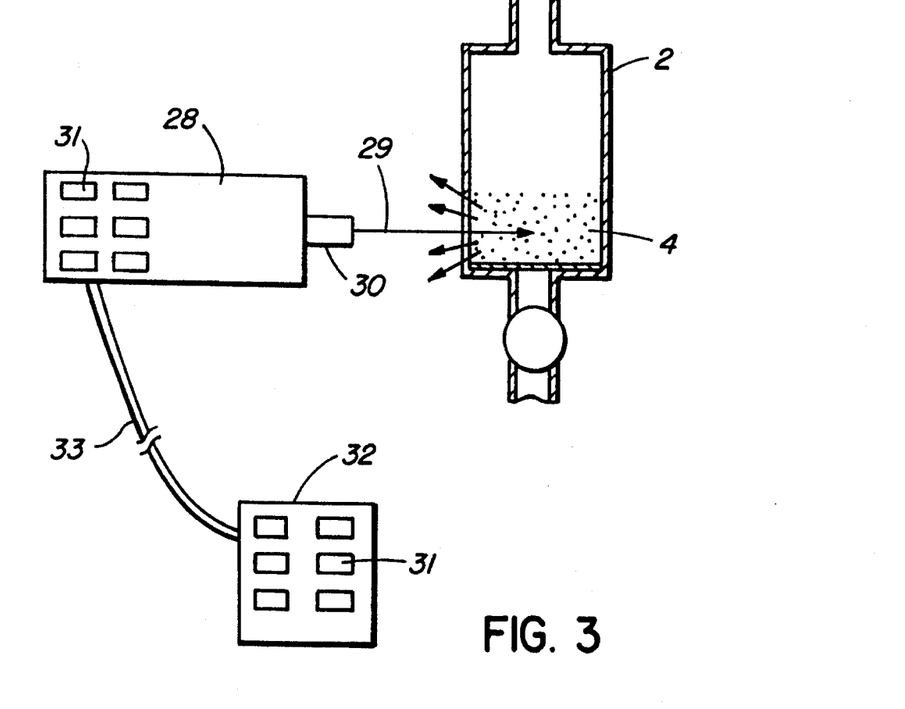
FIG. 3 is a schematic depiction of the equipment layout for effecting X-ray fluorescence analysis of a sample of trapping media containing an analyte.

The flow of water 1 is maintained until, gradually, the accumulation of trapped analytes reaches a concentration which will be convenient for analysis. Analysis is carried-out, in one variation, by transportation of the trapping media 4 to a laboratory where standard procedures are applied. Alternately, as shown in FIG. 3, x-ray fluorescence analysis may be effected in-situ.

Figure 2:
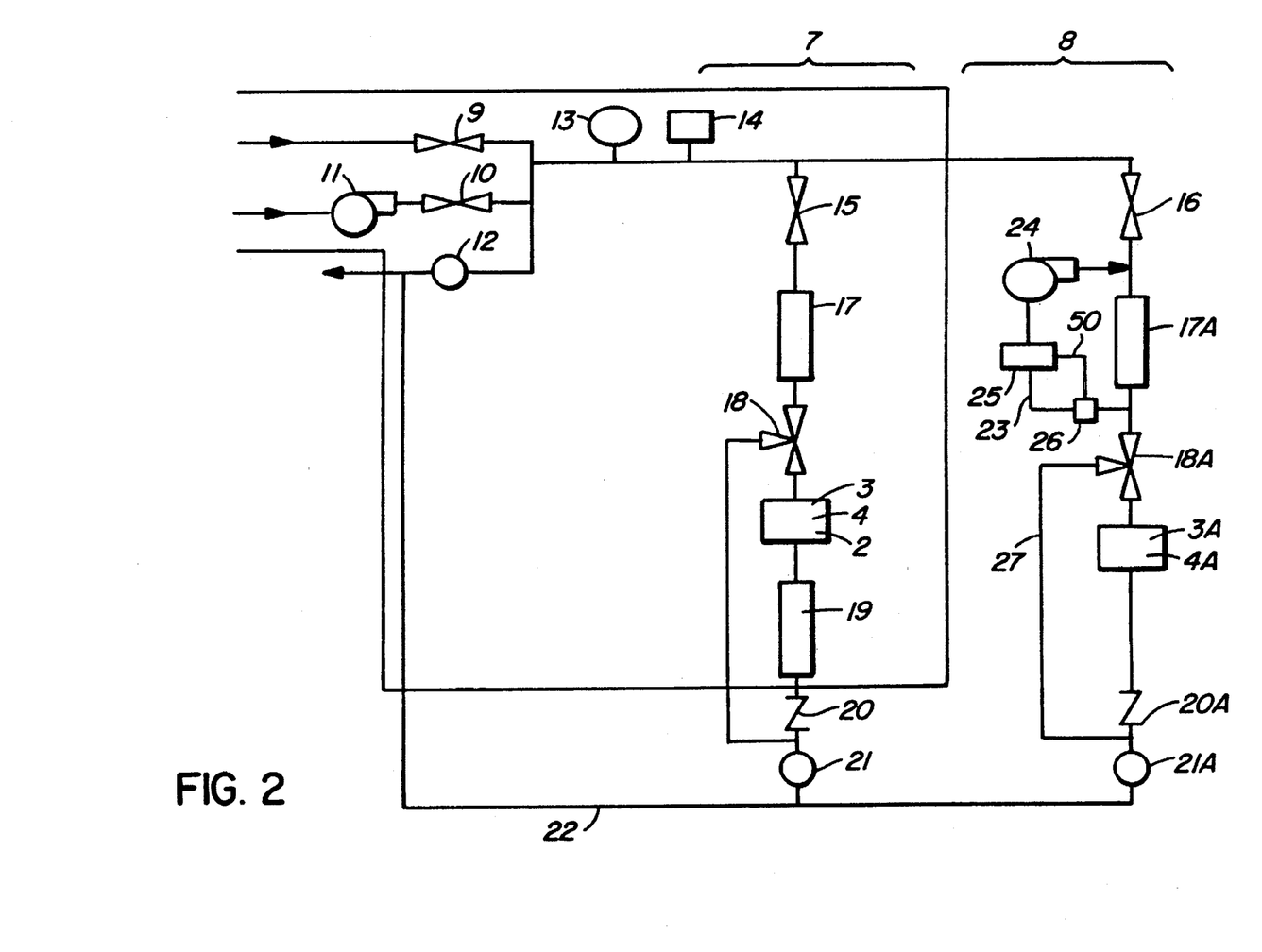
FIG. 2 is a more versatile version of the system of FIG. 1.

In FIG. 2 a more complex double filtering system is provided with two branches, a first combined organic and inorganic extraction branch 7, and a second inorganic extraction branch 8. Water may enter from a self-pressurized source through feed valve 9, or from an unpressurized source through a feed valve 10 wherein a pump 11 provides the pressure. A bleed valve 12 may be connected on the down-stream side of these valves to release water from the system.

A pressure meter 13 may be provided and an auto-shut-off pressure limiting valve 14 installed to protect system components from over-pressure conditions. Branch valves 15, 16 provide water access to the respective branches.

In the first, combined analysis branch 7, a mixer 17 may be included to incorporate "spiked" or injected standard quantities of a calibration compound into the water flow. A bypass valve 18 permits water to bypass the subsequent filter components for flushing-out the rest of the system and to allow for stabilization on a continuous flow basis to be established.

In branch 7 a cylinder 2 with filter column 3 according to the invention is provided, followed by a resin column 19. A check valve 20 passes the exiting water through a flow meter 21 to enter the return supply line 22. Up to the check valve 20 it is preferable to form all conduits from non-organic matter e.g. stainless steel, as branch 7 is intended to analyze for organic analytes.

In the inorganic branch 8, the mixer 17A is placed within a recirculating loop 23 powered by a recirculating pump 24 and incorporating an alkali reservoir 25 and pH sensor and controller 26. A controllable bypass valve 18A permits diversion of flow through a bypass 27, allowing a steady-state level of pH to be established for the water arriving at the bypass valve 18A. The pH level is established by control of the flow through the reservoir 25 in response to a preset target pH provided to the sensor 26. Control is effected through a link 50. Once the desired pH is established, flow is diverted through the trapping media 4A. Water then exits through check valve 20A, flow meter 21A and exits via the return supply line 22.

In the inorganic branch 8, organic conduits, such as polypropylene piping may conveniently be used.

The trapping media 4 in the combined branch 7 helps to avoid exposure of the resin column 19 to particulates. It also may be used to accumulate particulates and to trap a portion of the organics at the pH level of the infeed.

The trapping media 4A in the inorganic branch may be removed and replaced with fresh media 4 as different pH levels are established. The establishment of different pH levels will allow for maximized concentration of differing analytes that are pH sensitive.

In FIG. 3 an X-ray source 28 is located adjacent to the trapping media 4 in situ. The X-rays 29 penetrate the media 4 and are reflected back into a combined emitter/receiver 30 which detects the fluorescence generated in the media 4 by the X-rays 29. The receiver 30 provides an output 31, optionally at a remote location 32 via a communication link 33, which provides data on the identity and quantity of analytes, typically heavy metals, present in the trapping media 4. By including in the transmitted data sent to the receiver 30 the output of the water meter 21, 21A the display at the output 31 can be formatted in terms of the concentration of the measured analytes within the sampled water stream 1.

In FIG. 3, the X-ray source 28 may be provided with a pre-set level for the concentration of a target analyte before providing an output. This will ensure that results are obtained with a desired level of confidence and not prolonged unduly. This level may typically be 10 times the threshold level for detection.

When the pre-set level of concentration in the trapping media 4 has been reached, the X-ray source 28 may provide a signal that further sampling is no longer required. The sampling procedure may then be terminated. This may be effected by an automatic shut-off device that closes the relevant valves 9, 10.

Turning to details as to the trapping media 4, tests have been carried-out using both uncoated CELITE and CELITE which has been treated by exposure to 0.4 millimoles of aluminum hydroxide per gram of CELITE. Table 1 lists the recovery on untreated CELITE of amounts of trace metals from water to which the listed metals have been added, or "spiked", at a concentration of 20 parts per billion, with varying levels of pH.

TABLE 1

RECOVERY OF TRACE METALS BY UNCOATED CELITE
(20 ppb Spiked Ultra Pure Water Sample)
(averaged recoveries over 6+ tests)

| pH | Pb | Cu | Cd | Hg | Cr | As |
|---|---|---|---|---|---|---|
| 6 | 14.3 | 0.0 | 13.4 | 11.0 | 1.9 | 2.4 |
| 7 | 10.1 | 0.0 | 6.9 | 7.9 | 3.0 | 10.7 |
| 8 | 7.2 | 0.0 | 7.0 | 9.4 | 2.0 | 15.3 |
| 9 | 14.8 | 0.2 | 9.1 | 5.7 | 6.0 | 6.9 |
| 10 | 19.6 | 19.7 | 14.2 | 16.2 | 8.0 | 10.0 |
| 11 | 19.9 | 19.4 | 19.6 | 12.3 | 0.0 | 12.1 |
| 12 | 19.2 | 14.1 | 19.3 | 19.3 | 0.0 | 11.2 |

From Table 1 it is apparent that differing pH levels are suitable for maximizing the recovery of different metals. Further, the recovery ratios can be calibrated to permit projections to be made of the full content of analyte within a sample, when a standard proportion is recovered at a specific pH level.

Table 2 lists similar results for treated CELITE.

TABLE 2

PERFORMANCE OF COATED CELITE WITH VARIOUS HYDROXIDES
(Percentages of Metals Tapped In The Filter)

| Hydroxide Treatment | pH | Pb | Cd | As | Cr | Cu | Hg |
|---|---|---|---|---|---|---|---|
| Mg | 8 | 92.00 | 97.00 | 28.64 | 34.67 | 63.67 | 78.67 |
|  | 9 | 89.67 | 80.67 | 15.00 | 33.33 | 34.33 | 73.00 |
|  | 10 | 92.64 | 97.32 | 21.34 | 32.00 | 40.00 | 79.00 |
|  | 11 | 90.67 | 96.00 | 52.67 | 20.00 | 64.32 | 83.33 |
| Fe | 8 | 92.00 | 98.33 | 92.33 | 24.00 | 51.67 | 74.33 |

TABLE 2-continued

PERFORMANCE OF COATED CELITE
WITH VARIOUS HYDROXIDES
(Percentages of Metals Tapped In The Filter)

| Hydroxide Treatment | pH | Pb | Cd | As | Cr | Cu | Hg |
|---|---|---|---|---|---|---|---|
|  | 9 | 92.00 | 96.33 | 59.67 | 27.33 | 55.33 | 76.00 |
|  | 10 | 92.00 | 98.00 | 73.33 | 20.67 | 50.00 | 72.00 |
|  | 11 | 91.33 | 98.00 | 65.34 | 26.65 | 56.00 | 76.30 |
| Al | 8 | 92.00 | 51.67 | 29.00 | 17.33 | 2.33 | 64.60 |
|  | 9 | 91.67 | 82.67 | 22.00 | 10.65 | 9.67 | 63.67 |
|  | 10 | 91.69 | 97.65 | 18.00 | 14.00 | 25.00 | 72.30 |
|  | 11 | 92.00 | 98.64 | 99.30 | 16.00 | 81.00 | 82.33 |
| Spiked with analytes at a level of 30.00 ppb |||||||| 
| Measured Background Amount (ppb) |||||||| 
|  |  | 2.00 | 0.30 | 0.20 | 0.80 | 3.30 | 0.00 |

The coating procedure in respect of the media used to generate Table 2 was to dissolve an hydroxide, such as aluminum magnesium or iron hydroxide in water and then to impregnate the CELITE with the water. The CELITE is then dried by a flow of air to remove the superficial water and leave the pores impregnated with the hydrated hydroxide. It has been found preferable to use a freshly prepared hydroxide solution, and not one that is over 10 days old to obtain improved results. Tests have been effected with manganese hydroxide—$Mg(OH)_2$ and other divalent metal ion hydroxides such as iron, cobalt, nickel, copper and zinc are believed to be suitable. Further, trivalent metal ion hydroxides such as those of manganese, iron and chromium are also believed to be suitable.

A pesticide spiking experiment was carried out using 20L of ultra pure water. The spiking solution contained 20 uL of SUPELCO PESTICIDE MIXTURE and 1 ug of 4–4'dibromooctafluorobiphenyl (surrogate compound) in 100 mL of distilled water. A CELITE-based media was prepared as per the standard aluminum hydroxide treatment procedure and 20L of spiked water was allowed to pass through the system. The extract was analysed using GC-ECD and GC-MS. The results are shown in Table 3.

TABLE 3

EFFICIENCY OF RECOVERY FOR PESTICIDES

| PESTICIDE | SPIKED AMOUNT (ppt) | RECOVERY GC-ECD (%) | RECOVERY GC-MS (%) |
|---|---|---|---|
| BHC | 10 | 53 | 73 |
| BHC | 10 | 58 | 72 |
| BHC | 10 | 41 | 55 |
| Lindane | 10 | 52 | 65 |
| Heptachlor | 10 | 64 | 61 |
| Heptachlor Epoxide | 10 | 50 | 50 |
| Aldrin | 10 | 61 | 77 |
| Endosulfan I | 20 | 32 | 58 |
| Endosulfan II | 20 | 37 | 50 |
| pp-DDE | 20 | 62 | 73 |
| Dieldrin | 20 | 32 | 73 |
| Endrin | 20 | 50 | 75 |
| pp-DDD | 60 | 51 | 72 |
| Endrin Aldehyde | 60 | 70 | 59 |
| Endosulfan Sulfate | 60 | 193' | 61 |
| pp-DDT | 60 | 56 | 80 |

TABLE 3-continued

EFFICIENCY OF RECOVERY FOR PESTICIDES

| PESTICIDE | SPIKED AMOUNT (ppt) | RECOVERY GC-ECD (%) | RECOVERY GC-MS (%) |
|---|---|---|---|
| Surrogate | 50 | 56 | 61 |

'An unknown chlorocompound co-eluted

Table 4 shows the results of sampling 25 litres of Rideau River water in the vicinity of Ottawa, Canada. In this Table 4 the recovery is broken-down between the proportions of analyte detected on the trapping media 4 and the resin column 19. The CELITE of Table 4, as in the previous tests, had been treated with aluminum hydroxide as described above.

TABLE 4

ANALYSIS OF RIDEAU RIVER WATER
FOR PESTICIDES
Using Hydroxide-Enhanced CELITE
(parts per trillion)]

| PESTICIDES | TRAPPING MEDIA | RESIN COLUMN | TOTAL |
|---|---|---|---|
| DBCP | 1.90 | 0 | 1.90 |
| HCB | 0.80 | 0.17 | 0.97 |
| AIDRINE | 0.21 | 0.17 | 0.97 |
| op-DDE | 0.50 | 0.76 | 1.26 |
| CHLORDANE | 0.00 | 0.00 | 0.00 |
| pp-DDE | 0.10 | 0.00 | 0.10 |
| DIEDRIN + op-DD | 0.13 | 0.00 | 0.13 |
| pp-DDD + op-DDT | 0.34 | 0.41 | 0.75 |
| pp-DDT | 0.00 | 1.16 | 1.16 |
| PERMETHRINE | 55.93 | 14.31 | 70.24 |
| CYPERMETHRINE | 3.31 | 1.57 | 4.88 |

Comment: On-site sampling of Rideau River water.
Sample volume = 25 L

In Table 4 the pesticides are identified using the nomenclature of the United States Environmental Protection Agency "Analytical Reference Standards and Supplemental Data for Pesticides and Other Organic Compounds", document EPA-600/9-78-012, May 1978. Analysis was effected using gas chromatography for separation and then either mass spectroscopy or an electron capture detector for quantification.

Table 5 shows the recovery of a series of Polychlorodibenzo-p-Dioxins from a combined organic and inorganic analysis. A VARIAN'$^m$ brand gas chromatograph with an electron capture detector was used. The pH was at the natural level (circa pH=7). As a source of dioxins 10 litres of ultra pure water was spiked with 50 parts per trillion of dioxin mixtures (5 micrograms per millilitre each intoluene) supplied by Chromatographic Specialities Inc., 300 Laurier Blvd., Brockville, Ont., Canada, Cat. No. AM8280A. The components of the spiking mixture are listed in the first column of Table 5. Their concentrations in the 10 litre volume of ultra-pure are water. The second and third columns list percentage recoveries based on GC-ECD and GC-MS respectively.

TABLE 5

INVESTIGATION OF SYSTEM EFFICIENCY FOR POLYCHLORODIBENZO-p-DIOXINS (ON CPRT'S PLAIN CELITE FILTER AND RESIN COLUMN)[1]

| DIOXIN | TEST AMOUNT TRAPPED[1] FILTER/COLUMN | | TOTAL (ppt) | PERCENT RECOVERY | OTTAWA[2] RIVER (ppt) | OTTAWA[3] RIVER (ppt) |
|---|---|---|---|---|---|---|
| TCDD | 14.6 | | 24.9 | 39.5 | 78 | 20.8 | 15.1 |
| PnCDD | 4.5 | | 35.7 | 40.2 | 80 | 1.2 | 2.1 |
| HxCDD | 24.5 | | 129.4 | 153.9 | 308 | 3.2 | 0.8 |
| HpCDD | 6.8 | | 29.0 | 35.8 | 72 | 0.4 | 2.3 |
| OCDD | 10.4 | | 35.9 | 46.3 | 93 | 1.0 | 5.1 |
| pH 7 | | | | | | |

[1] 10 L ultrapure water spiked at 50 ppt level
[2] 30 L of river water was sampled at a site downstream of the Eddy/Scott Paper Mills
[3] A 10 L Grab sample was pumped through a system at CPRT Laboratories Results obtained using Kieselghur that had been impregnated with $Al(OH)_3$ at a level of 0.2 mmole $Al(OH)_3$ per gram of Kieselhur at pH 11 as the trapping media are as follows in Table 6:

TABLE 6

RECOVERY OF METALS (KIESELGHURC AS TRAPPING MEDIA)

| Metals | Pb | Cd | Cr |
|---|---|---|---|
| Amount of spike (ppb) | 20 | 20 | 20 |
| Amount recovered | 20 | 19.8 | 7.7 |
| % Recovery | 100 | 99 | 38.5 |

Table 7 shows a comparison of the performance of a series of filter media in terms of the volumes of water that may be sampled before significant back-pressure from filter plugging develops.

Figure 4:
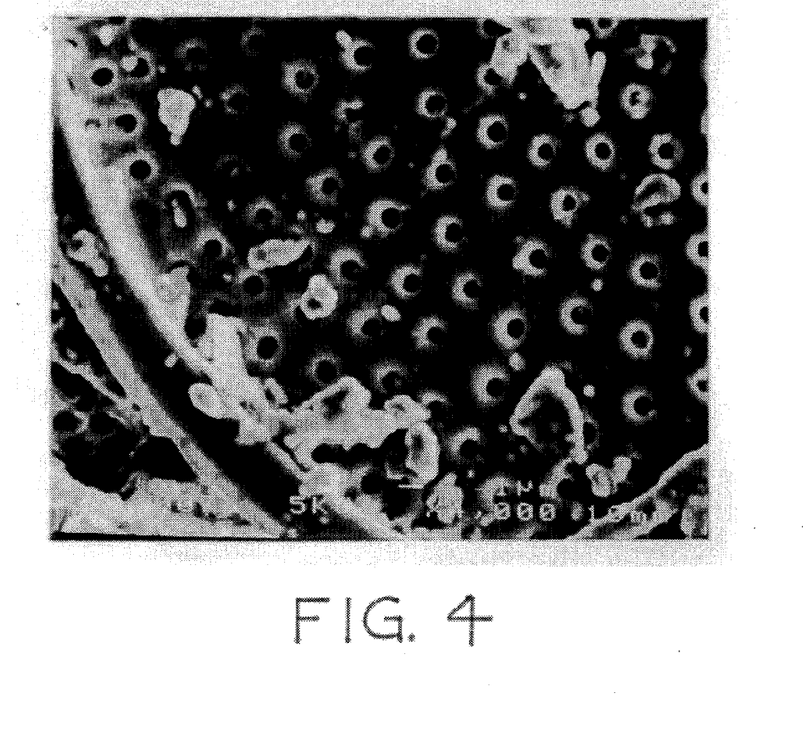
FIG. 4 is a photograph of the surface of uncoated CELITE particles.
Figure 5:
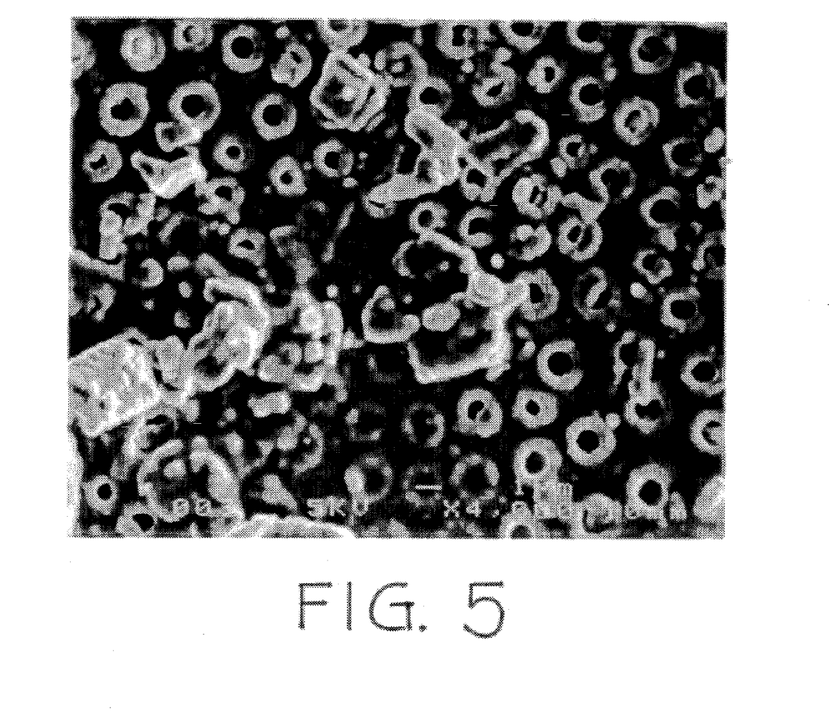
FIG. 5 is a photograph of the surface of CELITE when coated with aluminum hydroxide.
Figure 6:
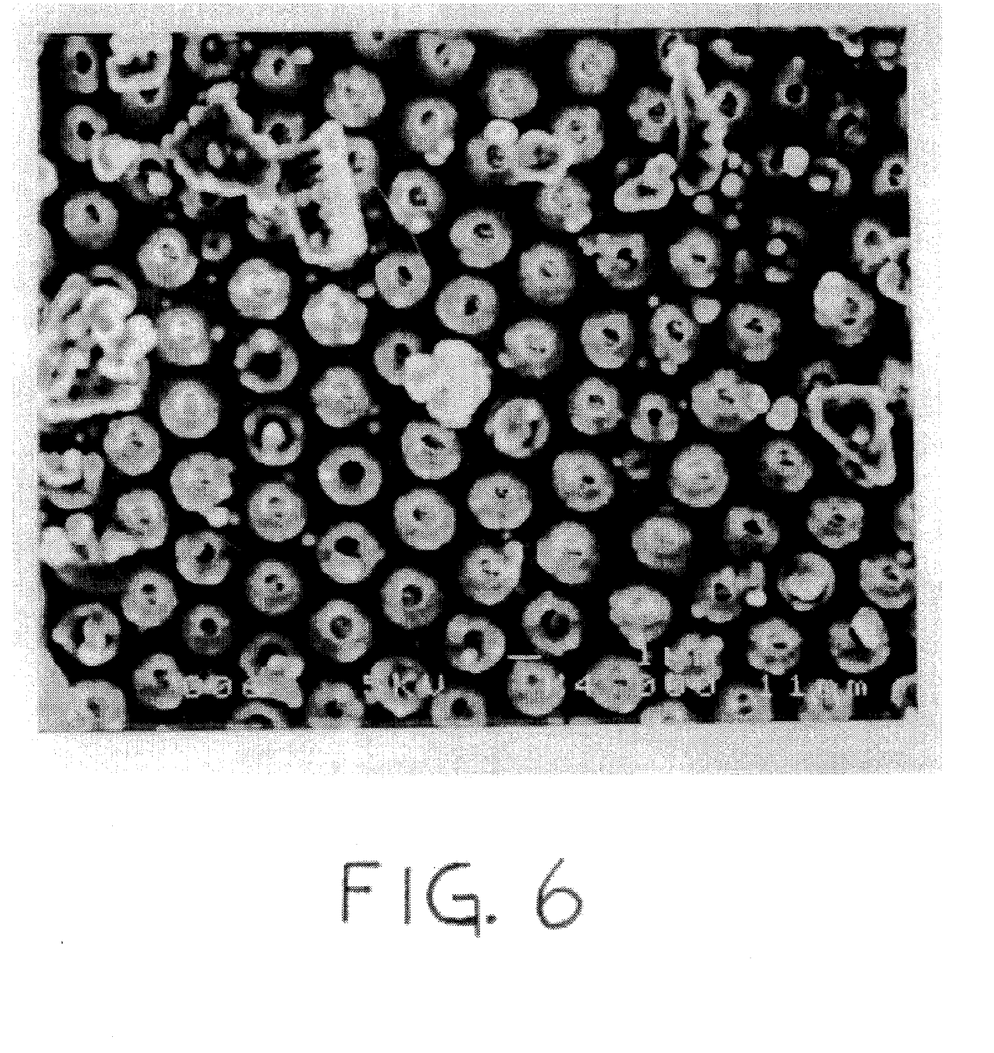
FIG. 6 is a photograph of the coated CELITE surface which has accumulated deposits of spiked heavy metals in the CELITE pores.

FIGS. 4–6 show electron microscope scans of CELITE at a magnification of 4000. FIG. 4 shows uncoated CELITE. FIG. 5 shows CELITE coated with 0.2 mmoles per gram of aluminum hydroxide on CELITE. FIG. 6 shows the same type of treated sample of CELITE after it has been exposed to water containing 20 ppb/litre quantities each of arsenic, copper, chromium, cadmium, mercury and lead. The greater degree of occlusion of the pores in FIG. 6 over those of FIG. 5 is apparent.

Figure 7:
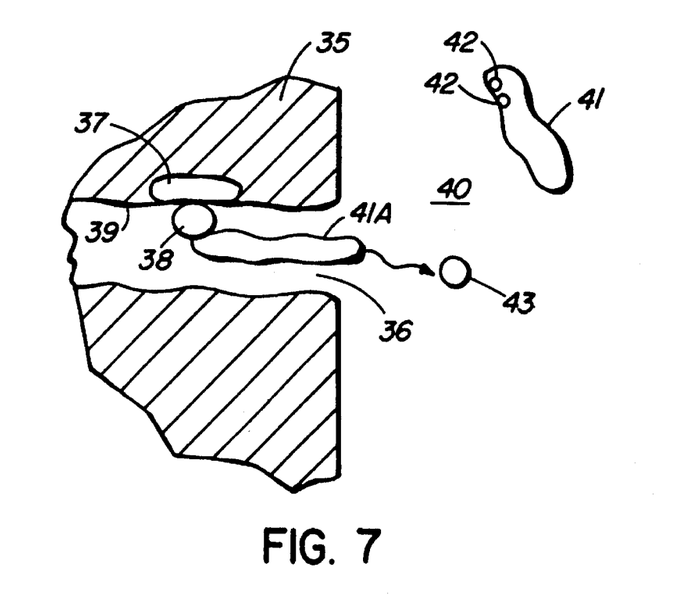
FIG. 7 is a schematic depiction of the entrapment of a colloid on the surface of the trapping media of the invention.

While not wishing to be bound by the following, FIG. 7 depicts one theory of the operation of the trapping media of this invention. In FIG. 7 the wall 35 of a portion of microporous trapping media 4, such as diatomaceous earth, surrounding a pore 36 is shown in cross-section. Along the inside surface 39 of the pore 36, an hydroxide complex 37 presents an "active" hydroxide group 38 outwardly from the inner surface 39. In the adjacent, surrounding water 40, colloidal gel carriers 41 are present to which are adhered analytes 42. The colloidal carrier 40 upon entering the pore

TABLE 7

FILTER PERFORMANCE

| Run # | Flow Rate mL/min | Filter 4.7 cm dia. | Turbidity NTU Input/Output | Pressure psi | Volume L |
|---|---|---|---|---|---|
| 1. | 200 | W-934-AH 1.5 um | 0.15/0.13 | 20 | 10 |
| 2. | 200 | W-GF/F 0.7 um | 0.15/0.08 | 20 | 4 |
| 3. | 100 | CAMBRIDGE 1.0 um | 0.15/0.13 | 20 | 40 |
| 4. | 200 | CAMBRIDGE 1.0 um | 5.0/2.0 | 20 | 4 |
| 5. | 100 | ACTIVATED CARBON | 10.0/1.45 | 25 | 10 |
| 6. | 100 | CELLULOSE | 10.0/0.6 | 25 | 1 |
| 7. | 100 | SILICA GEL | 5.0/<1.0 | 25 | 1 |
| 8. | 100 | GAC | 5.0/<1.0 | 25 | 2 |
| 9. | 100 | SEPHADEX | 5.0/<1.0 | 25 | 1 |
| 10. | 100 | CELITE (unmodified) | 0.15/0.10 | 5 | 100 |
| 11. | 200 | CELITE (unmodified) | 5.0/0.4 | 1 | 20 |
| 12. | 200 | CELITE (unmodified) | 10.0/0.67 | 10 | 20 |
| 13. | 200 | CELITE (unmodified) | 10.0/0.50 | 9 | 60 |
| 14. | 100 | CELITE (unmodified) | 10.0/0.67 | 5 | 30 |

1. W-934-AH 1.5 um Filter Paper from the Cambridge Filter Paper Company.
2. W-GF/F 0.7 um Filter Paper from the Cambridge Filter Paper Company.
3. Cambridge 1.0 um Filter Paper from the Cambridge Filter Paper Company.
4. Cambridge 1.0 um Filter Paper from the Cambridge Filter Paper Company.
8. GAC Granular Activated Cabron supplied by Aldrich Chemicals, U.S.A.
9. SEPHADEX Gel Filtration Resin supplied by Aldrich chemicals, U.S.A.

36, is believed to form new bonds with the hydroxyl group 38, releasing hydrogen ions 43. This irreversibly fixes the colloid 41a to the trapping media 4 to a degree not present with adsorbers.

The analytes 42 are entrained within the colloids 41 and become similarly entrapped. They are then available for analysis by the customary procedures.

It has also been found that CELITE (tm) in particular will trap bacteria and protozoa and, it is believed, diatoms and other multicell microbiota. Samples of giardia and cryptospirodium protozoa, and salmonella bacteria have been concentrated in the CELITE filter medium. The effectiveness of filter media of the invention in effecting such a concentration may be due in part to the presence of a charge distribution on such organic micro-organisms.

Once concentrated in the filter medium by whatever mechanism, a washing solution taken from the medium was able to innoculate gel and produce cultures of these bacteria. Accordingly, the invention extends to the concentration of such micro-organisms as a class of analytes.

CONCLUSION

The foregoing has constituted a description of specific embodiments showing how the invention may be applied and put into use. These embodiments are only exemplary. The invention in its broadest, and more specific aspects, is further described and defined in the claims which now follow.

The Embodiments of the Invention in which an exclusive property or privilege is claimed are defined as follows:

1. A method for analyzing water for the presence of an analyte in the presence of colloids, comprising the steps of:
   (1) exposing micorporous, inorganic trapping media having internal surfaces which bear active, hydrated hydroxyl groups thereon to a measured volume of continuously flowing non-saline water under alkaline conditions containing metal colloids and an analyte entrained therein at ultra trace levels being a concentration of less than one part per billion,
   (2) allowing said, hydrated hydroxyl groups to immobilize said colloids on said surfaces to progressively accumulate a coating of colloids as a gel through the release of hydronium/hydrogen ions, until a measurable quantity of analytes is deposited within the trapping media; and
   (3) analyzing said trapping media to determine the identity and quantity of analyte therein.

2. A method as in claim 1 wherein the trapping media comprises diatomaceous earth.

3. A method as in claim 1 wherein the process of analyzing is effected by means for spectroscopic or chromatographic analysis of the analyte, the steps of exposing the trapping media to water and analyzing the trapping media for the anlayte being performed in-situ, from prior to the detection of said analyte until the presence of the analyte is detected at a level sufficient to determine its identity and quantity.

4. A method as in claim 3 wherein the trapping media has a hydrated metal hydroxide deposited therein.

5. A method as in claim 1 wherein the trapping media has a hydrated metal hydroxide deposited therein.

6. A method as in claim 5 wherein the metal hydroxide is selected from the group consisting of aluminum hydroxide, magnesium hydroxide and iron hydroxide.

7. A method as in claim 1 further comprising a step of adjusting the pH of said water to cause said metal to precipitate out of solution and become entrained within said colloids.

8. A method as in claim 7 wherein the trapping media comprises diatomaceous earth.

9. A method as in claim 7 wherein a pH adjusting substance is provided in association with the trapping media to locally adjust the pH to effect the precipitation of the dissolved metals from solution in the vicinity of the trapping media.

10. A method as in claim 9 wherein the trapping media is diatomaceous earth having a hydrated metal hydroxide deposited therein.

11. A method as in claim 10 wherein the metal hydroxide is selected from the group consisting of aluminum hydroxide, magnesium hydroxide and iron hydroxide.

12. A method as in claim 10 wherein the diatomaceous earth has been calcined prior to having the hydrated metal hydroxide deposited therein.

13. A method for analyzing water for the presence of an analyte in the presence of colloids, comprising the steps of:
   (1) preparing microporous, inorganic trapping media having internal surfaces to provide active, hydrated hydroxyl groups thereon by impregnating the media with an aqueous metal hydroxide solution;
   (2) exposing said media to a measured volume of continuously flowing non-saline water under alkaline conditions containing metal colloids and an analyte entrained therein;
   (3) allowing said, hydrated hydroxyl groups to immobilize said colloids on said surfaces to progressively accumulate a coating of colloids as a gel through the release of hydronium/hydrogen ions until a measurable quantity of analytes is deposited within the trapping media; and
   (4) analyzing said trapping media to determine the identity and quantity of analyte therein.

14. A method as in claim 13 wherein the analyte is entrained in the following, non-galine water at trace levels, being a concentration of less than one part per billion.

15. A method as in claim 13, comprising the steps of analyzing water containing a metal in solution as the analyte and adjusting the pH of the water by means of a pH adjusting substance to cause such metal in solution to come out of solution and become entrained within said colloids.

16. A method as in claim 15 wherein a pH adjusting substance is provided in association with the trapping media to locally adjust the pH to effect the precipitation of the dissolved metals from solution in the vicinity of the trapping media.

17. A method as in claim 13 wherein the trapping media comprises diatomaceous earth.

18. A method as in claim 17 wherein the diatomaceous earth has been calcined prior to being impregnated with the aqueous metal hydroxide solution.

* * * * *